(12) United States Patent
Batich et al.

(10) Patent No.: US 6,602,524 B2
(45) Date of Patent: Aug. 5, 2003

(54) MICROSPHERES FOR USE IN THE TREATMENT OF CANCER

(75) Inventors: Christopher D. Batich, Gainesville, FL (US); Adam Leckey, Palm Beach Gardens, FL (US); J. Nicolas Vauthey, Houston, TX (US)

(73) Assignee: University of Florida, Gainesville, FL (US)

(*) Notice: Subject to any disclaimer, the term of this patent is extended or adjusted under 35 U.S.C. 154(b) by 13 days.

(21) Appl. No.: 09/928,289

(22) Filed: Aug. 10, 2001

(65) Prior Publication Data

US 2002/0009415 A1 Jan. 24, 2002

Related U.S. Application Data

(63) Continuation of application No. 09/143,774, filed on Aug. 31, 1998, now abandoned.

(51) Int. Cl.[7] ............... A61K 9/14; A61K 9/16; A61K 9/50
(52) U.S. Cl. ............ 424/489; 424/490; 424/497; 424/501
(58) Field of Search ............ 424/489, 490, 424/497, 501

(56) References Cited

U.S. PATENT DOCUMENTS

| | | | |
|---|---|---|---|
| 4,321,117 A | * 3/1982 | Kaetsu et al. | 204/159.16 |
| 4,536,387 A | 8/1985 | Sakamoto et al. | |
| 4,584,368 A | 4/1986 | Rubin | |
| 4,642,111 A | 2/1987 | Sakamoto et al. | |
| 4,997,913 A | 3/1991 | Hellstrom et al. | |
| 5,122,368 A | 6/1992 | Greenfield et al. | |
| 5,306,809 A | 4/1994 | Boon et al. | |
| 5,654,006 A | * 8/1997 | Fernandez et al. | 424/489 |

FOREIGN PATENT DOCUMENTS

WO      WO-95/13798      *  5/1995

OTHER PUBLICATIONS

Siegel et al pH–Dependent Equilibrium Swelling Properites of Hydrophobic Polyelectrolyte Copolymer Gels Macromolecules 21:3254–3259 1988.*

Leckey Active Microspheres for use in the Treatment of Hepatic Tumors Thesis presented to the Graduate School of the University of Florida 1997.*

Leckey, A. "Active Microspheres for Use in the Treatment of Hepatic Tumors" A thesis presented to the graduate school of the University of Florida in partial fulfillment of the requirements for the degree of Master of Science, 1997.

Ksontini, R. et al. "Regional Therapy for Liver Tumors: A Novel Embolic Agent and Drug Delivery System" UF Shands Cancer Center GI Cancer Letter, Winter 1997, vol. 4, No. 1.

Ichihara, T. et al. "Transcatheter Arterial Chemoembolization Therapy for Hepatocellular Carcinoma Using Polylactic Acid Microspheres Containing Aclarubicin Hydrochloride" *Cancer Research*, Aug. 1, 1989, vol. 49:4357–4362.

Baker, M.A. et al. "Zyn–linked colchicines: Controlled–release lipophilic prodrugs with enhanced antitumor efficacy" *Journal of Controlled Release*, 1996, vol. 40:89–100.

Bhattacharya, S. et al. "Iodized oil in the treatment of hepatocellular carcinoma" *British Journal of Surgery*, 1994, vol. 81:1563–1571.

* cited by examiner

*Primary Examiner*—Thurman K. Page
*Assistant Examiner*—Todd D Ware
(74) *Attorney, Agent, or Firm*—Saliwanchik, Lloyd & Saliwanchik

(57) ABSTRACT

The subject invention pertains to novel materials and methods for use in treating patients afflicted with oncological disorders, such as tumors. One aspect of the invention concerns methods for treating tumors comprising the administration of drug loaded pH-sensitive microspheres to a patient in need of anticancer therapy. The pH-sensitive microspheres have a swelling transition with the pH range found in or near tumor tissue. When the microspheres swell, the loaded drug is released into the microenvironment of the tumor tissue. The subject invention also pertains to novel microspheres useful in the methods of the invention. The microspheres are capable of effectively releasing a loaded substance at a pre-determined pH. The subject invention also concerns novel methods for synthesizing the microspheres of the present invention.

21 Claims, 4 Drawing Sheets

MICROSPHERES FOR USE IN THE TREATMENT OF CANCER

CROSS-REFERENCE TO RELATED APPLICATION

This application is a continuation of U.S. application Ser. No. 09/143,774, filed Aug. 31, 1998, now abandoned.

BACKGROUND OF THE INVENTION

With advances in antibiotics and vaccines there has been a reduction in the seriousness of many infectious diseases; however, cancer still remains as a mostly incurable threat. In fact, cancer accounts for about 10 percent of all deaths in the U.S. every year (Oppenheimer, 1985). One obstacle in the treatment of cancer is that the basic mechanism of cancer development and propagation is not well understood and, therefore, investigation into possible cancer treatments may require knowledge from a variety of different disciplines (Braun, 1974, Muir, 1988). Cancer patients must withstand the debilitating mental and physical effects throughout the long duration of the disease which also results in an economic burden to both the patient and the community (Busch, 1974).

The mortality rate for patients diagnosed with either primary or secondary liver cancer is very high. Many new approaches towards possible treatments are currently being investigated; however, successes have been minimal and surgery still remains as the best form of treatment, even though less than 10 percent of the patients are suitable for this option (Kemeny et al., 1995). Non-surgical forms of treatment include various routes of chemotherapy in which toxic chemotherapeutic drugs are delivered to the liver tumors, either systemically (throughout the entire body) or regionally (directly into the liver). The chemotherapeutic drugs such as fluorodeoxyuridine (FUDR) and doxorubicin (adriamyacin) work by having a greater toxic effect on actively dividing cells such as cancer cells, rather than most normal tissues. The goal in this form of treatment is to deliver a high dose of the drug to the tumor tissue while keeping the concentration of the drug (and its toxic effects) in normal tissue to a minimum. The toxic side effects of the chemotherapeutic agents may be the limiting factor in determining the drug concentration delivered to the patient. In many cases there is insufficient killing of the tumor cells and regrowth and spreading may occur (Bhattacharya et al., 1994). In addition, with conventional systemic or regional treatment, the excess drug which does not contact tumor tissue degrades the condition of the healthy tissue and, therefore, can become the limiting factor in dose concentration (Kemeny et al., supra). An ideal situation would occur if the toxic effects of the drugs could be completely localized within the liver tumor tissue without affecting the surrounding healthy tissue, enabling a higher drug concentration to completely kill all of the cancer cells.

Chemotherapy is often combined with another form of treatment termed embolization in which the blood supply to the tumor is essentially reduced or stopped either temporarily or permanently in an attempt to arrest the tumor growth or cause regression. Typical embolic agents include steel coils as well as polyvinyl alcohol sponge (IVALON), collagen, gelatin sponge (GELFOAM), albumin, and starch materials that may be in the form of microspheres or particles. Because healthy liver tissue has a dual blood supply through the hepatic artery and the portal vein, and most hepatic tumors are oxygenated almost exclusively from the hepatic artery, the theory behind embolization is that this artery can be obstructed by injections of these materials in an attempt to starve the tumor of its blood supply without injury to the majority of the liver. If this technique is used in combination with regional chemotherapy the drug can be contained within the tumor tissue for longer periods of exposure time (Lin et al., 1988, Kemeny et al., 1995). In many cases, however, a collateral circulation will appear and circumvent the blockage or the embolized artery will reopen allowing blood to once again feed the tumor. If viable tumor cells still remain, this will allow them to regrow tumor tissue (Kemeny et al., 1995).

Natural and synthetic polymers have been used to produce microspheres for a variety of biomedical applications including general and targeted drug delivery devices. The term microsphere generally refers to spherical particles between 2 nm to 50 nm in diameter but smaller sizes (usually below 1 micrometer) may be referred to as nanospheres. Micro particles are similar but usually irregular in shape (Arshady, 1993). As mentioned previously, some polymeric spheres and particles have been used as embolic agents for the treatment of liver cancer. These materials, such as starch, poly (vinyl alcohol), and gelatin, do not release a drug but rather serve to occlude the blood flow after a drug has already been delivered in order to allow increased retention time within the liver (Lin et al., 1988). Work has also been done in the development of polymeric microspheres that deliver anticancer drugs in a controlled fashion. For example, a feasibility study was done for the oral delivery of an anticancer drug, methotrexate, encapsulated in degradable gelatin microspheres. The microspheres were coated with the natural polymers chitosan and alginate which would enable the microspheres to pass through the gastrointestinal tract to reach the intestine where the drug action or absorption is desired. In theory, higher concentrations of the toxic drug could be delivered using this targeted delivery system rather than systemic treatment while reducing side effects which include vomiting, diarrhea, gastro intestinal ulceration, and liver and kidney damage (Narayani et al., 1995). Experiments by Kato et al. (1981) showed that mitomycin C or cisplatin could be encapsulated within biodegradable ethyl-cellulose microcapsules for possible use in chemoembolization, and a separate study showed that cisplatin could be loaded into poly(lactide) microspheres such that continuous release could be obtained for a period of several days to a week. Cisplatin is one of the most potent chemotherapeutic agents known and is commonly used to treat liver tumors. Since the drug can cause many toxic side effects, the use of microspheres has been suggested to target its action by hepatic arterial injection and controlled release (Spenlehauer et al., 1986). This idea is supported by a separate study using a rat model that showed microspheres of a certain size range delivered to the liver via the hepatic artery were found to be concentrated in a 3:1 ration of tumor tissue to liver tissue for implanted salivary adenocarcinomas (Meade et al., 1987). While these degradable microsphere systems would be able to achieve continuous release within the liver, they remain non-tumor specific and drug concentrations would ultimately be limited by the toxic side effects produced, including damage to healthy liver tissue (Kemeny et al., 1995). One current area of research that attempts to increase the targeting of anticancer treatment is with the use of magnetically directed microspheres. Hafeli et al. (1994) have developed poly(lactic acid) microspheres which can be loaded with Yttrium-90 and incorporated with magnetite such that it may be possible to magnetically direct the radiotoxic effect of the spheres to be more concentrated near tumor sites.

Malignant cells show an increased rate of glucose uptake and aerobic glycolysis with the resulting formation of lactic acid (Volk et al., 1993). In normal cells the uptake of glucose is accomplished by membrane proteins known as glucose transporters. Depending on the cell type, the proteins show different patterns of expression, hormone responsiveness, and transport properties. When cells transform into the malignant state the number of the glucose transporter proteins per cell is commonly increased. Because of this, the uptake of glucose into malignant cells is no longer regulated by systemic or cellular demands, and is instead controlled almost completely by the extracellular concentrations (Jahde and Rajewsky, 1982). This means that the increased amounts of lactic acid produced by the aerobic metabolism can be further increased by the systemic infusion of glucose, resulting in local tumor pH values that are lower than that for healthy tissue (which remains consistently close to 7.4) (Volk et al., 1993).

As can be understood from the above, there remains a need for a drug delivery system for cancer treatment, such as primary or secondary liver cancer, that would release an anticancer agent in high concentrations only within the tumor tissue while healthy tissue would remain relatively unaffected.

BRIEF SUMMARY OF THE INVENTION

The subject invention pertains to novel materials and methods for use in treating patients afflicted with malignancies. Specifically exemplified is a method of treating hepatic tumors comprising the use of drug loaded pH-sensitive microspheres. In one embodiment, pH-sensitive microspheres of the invention exhibit a swelling transition within the pH range typically found in tumor tissue. The materials and methods of the subject invention provide a novel treatment of cancer which specifically targets tumor tissue and reduces the damage to surrounding healthy tissue. Further, the subject invention provides a viable alternative to surgical techniques, in addition to reducing the amount of adverse side effects such as vomiting, myelosuppression, cardiac toxicity, pulmonary fibrosis, hepatobiliary toxicity, and pericholangitis commonly associated with other current non-invasive treatments.

One aspect of the subject invention is directed towards methods of treating a tumor comprising administering an effective amount of microspheres that are capable of releasing a substance at a pre-specified pH. The substance contained in the microspheres can include, but is not limited to, cytotoxic agents, chemotherapeutic agents, and radionuclides.

The subject invention also pertains to novel microspheres that can be loaded with a substance useful in treating cancerous cells. The microspheres are capable of effectively releasing the loaded substance at a pre-determined pH. The microspheres can be designed to release their substance over a period of time at a pH that is typically found in or near cancerous tissue.

The subject invention also concerns methods for preparing microspheres of the present invention. The methods of the invention allow for the preparation of microspheres whereby the amount of a selected substance to be loaded in a microsphere, as well as the release characteristics of the microspheres, e.g., release/time curve and pH, can all be selected for and manipulated.

BRIEF DESCRIPTION OF THE DRAWINGS

In FIG. 1, the microspheres showed complete release at a pH of 6.0 after 13 days, and less than 50% release at pH 6.5 and 6.8 after the full 14 days. FIGS. 2 and 3 show that by increasing the DEA content (as well as decreasing the amount of crosslinking) of the spheres, an increase in the overall release kinetics results.

In FIG. 7, the curves virtually overlap which shows that at pH 6.5 the microsphere swelling is such that the dye release has little or no dependence on the sphere size. However, in FIG. 8, which shows release at pH 6.7, the 80–150 $\mu$m diameter spheres show a noticeably slower release with a 14 day total of only 86% compared to 98% for the smaller spheres.

DETAILED DISCLOSURE OF THE INVENTION

Figure 1:
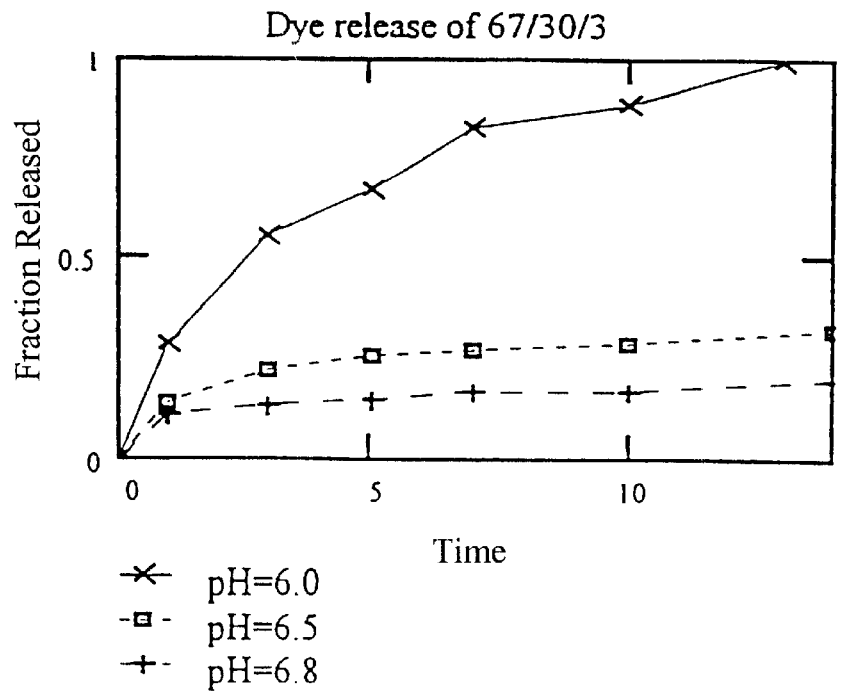
FIGS. 1–3 show the release of the test dye over a 14 day period at pH 6.0, 6.5, and 6.8 for the 67/30/3, 65/34/1, 60/38.5/1.5 ethyl methacrylate (EMA)/(diethyl amino)ethyl methacrylate (DEA)/divinyl benzene (DVB) microsphere compositions.

The subject invention pertains to novel methods and compositions for treatment of cancer. In one embodiment, the invention provides methods of treatment utilizing pH-dependent microspheres which release a drug or other therapeutic agent within a predetermined pH range. The microspheres are prepared so that the therapeutic agent is released near cancer or tumor cells due to the lower pH within the microenvironment surrounding those cells. The methods and materials of the subject invention can also be used to treat other diseases where pH of the microenvironment in and around the diseased tissue or cells is lower than in non-diseased tissue or cells.

The subject invention utilizes a pH-sensitive, non-degradable carrier (microsphere) having a matrix that can swell as a result of the lower pH associated with the physiological microenvironment of, for example, a tumor resulting in the gradual release of a selected substance contained within the microsphere, such as a chemotherapeutic agent. In this manner, release of the substance from the microsphere is localized within the tumor tissue, with minimal release occurring elsewhere in the surrounding tissue where the pH is at normal levels. In one embodiment, depending on the tumor pH, glucose can be infused to create a further increase in the $H^+$ ion activity of the tumor tissue, resulting in an increased release rate of the agent from the swollen microsphere matrix. The microspheres can be injected via a blood vessel proximate to the tumor, e.g., the hepatic artery in liver tumors, such that injected microspheres are lodged preferentially within the tumor tissue. This allows a drug concentration to be released that is substantially greater than that delivered by other techniques without the associated high level of toxicity affecting the healthy tissue. In one embodiment, microspheres are designed to release substantially all of their contents over about a two week period at a pH range of about 6.7 to 6.8.

The subject invention pertains to a method of treating cancer by administering an effective amount of microspheres containing a selected substance or substances, wherein the microspheres can release the substance(s) at a selected pH. Substances for use with the microspheres of the present invention include, but are not limited to, cytotoxic agents, chemotherapeutic agents and radionuclides. In a specific embodiment, administration of an effective amount of microspheres includes the injection of the microspheres in a blood vessel, such as an artery, proximate or upstream of a metastasis, or tumor. Microspheres can be loaded with a selected substance or substances by contact with a solution containing the substances. Loading can also include the steps of prewashing the microspheres with an organic solvent, contacting the microspheres with a solution containing the substance(s), and washing the loaded microspheres with water. The microspheres can be loaded by other suitable methods known to those skilled in the art.

A preferred embodiment of the subject invention pertains to a method of treating a tumor comprising preparing pH-dependent microspheres which contain a selected anti-tumor substance and injecting the microspheres in a blood vessel suitable for carrying the microspheres to the tumor.

Another aspect of the subject invention pertains to novel non-degradable microsphere compositions useful for pH-regulated release of therapeutic agents, such as anti-neoplastic drugs. The microspheres can be loaded under conditions where a substance is incorporated within the matrix. The loaded microspheres can then release the substance when exposed to a certain pH range. In one embodiment, the microspheres of the subject invention are designed to release the substance contained within the microspheres over a period of time when exposed to a pH typically associated in the microenvironment of cancerous tissue. Preferably, the microspheres are loaded with any substance suitable to treat cancer cells such as cytotoxic agents, chemotherapeutic agents, and radionuclides. The microspheres of the subject invention can be made of any materials known by those skilled in the art that can swell and collapse under particular conditions, e.g., cross-linked polymer gels that possess either weakly acidic or basic pendant groups. Preferably, the matrix of the gels is composed of a co-polymer containing a hydrophobic component and a less hydrophobic ionizable component which are then lightly cross-linked.

The composition of the subject microspheres can comprise one or more of the following: poly(n-alkyl methacrylate-co-diethylaminoethyl methacrylate); poly (sterene-co-vinyl pyridine), "PSVP"; divinylbenzene, "DVB"; hydrophobic N-alkyl methacrylate, such as n-butyl methacrylate; (dimethylamino)ethyl methacrylate, "DMA"; diethyl(aminoethyl) methacrylate, "DEA"; ethyl methacrylate, "EMA"; poly(vinyl pyrrolidone), "PVP"; poly (ethylmethacrylate), "PEMA"; and poly (methylmethacrylate), "PMMA." In one embodiment, the microspheres of the subject invention comprise ethyl methacrylate, diethylaminoethyl methacrylate, and divinyl benzene. Preferably, the mole percent ratios of ethyl methacrylate, diethylaminoethyl methacrylate, and divinyl benzene are about 65 to about 50, about 34 to about 49, and about 1 to about 3, respectively. Most preferably, the microspheres of the subject invention have mole percent ratios of ethyl methacrylate, diethylaminoethyl methacrylate, and divinyl benzene of about 50:49:1, respectively.

The present invention also concerns methods for preparing microspheres of the subject invention. In one embodiment, the method comprises preparing a monomer solution comprising ethyl methacrylate, diethylaminoethyl methacrylate, and divinyl benzene; mixing the monomer solution; and heating the monomer solution. In a specific embodiment, the monomer solution is prepared by mixing ethyl methacrylate, diethylaminoethyl methacrylate, and divinyl benzene having mole weight ratios of about 50 to about 65, about 34 to about 49, and about 1 to about 1.5, respectively, with recrystallized azobisisobutyronitrile (AIBN). In a preferred embodiment, the method for preparing microspheres can further comprise cleaning and drying the microspheres.

A specific embodiment of the subject invention pertains to microspheres useful in the medical treatment of a disease, where the microspheres are capable of being loaded with a substance and then effectively releasing the incorporated substance when exposed to a predetermined pH. Preferably, the microspheres of the subject invention are constructed so as to release the loaded substance at a pH of from about 6.0 to about 7.4. More preferably, the release pH can be from about 6.3 to about 7.0. Most preferably, the release pH can be from about 6.5 to about 7.0. As used herein, the term "effectively releasing" is intended to mean an extended release at the selected pH suitable for treating a tumor. In one embodiment, the microspheres are capable of effectively releasing about 50% of their loaded substance after 14 days at a pH of about 6.8. The microspheres can have a loading capacity of up to about 20% of their weight. In one embodiment, the microspheres of the subject invention have a weight percentage of loading of up to about 16.6%.

The microspheres can be constructed in sizes suitable for particular applications. The size is typically selected as a size that is small enough to allow the microsphere to be located close to the diseased or cancerous cells or tissue but not so small that the microspheres will pass through the circulatory system to other areas of the body. In one embodiment, the microspheres of the subject invention range in size from about 10 $\mu$m to about 150 $\mu$m in diameter. In a preferred embodiment, the microspheres are from about 25 $\mu$m to about 35 $\mu$m in diameter.

Following are examples which illustrate procedures for practicing the invention. These examples should not be construed as limiting. All percentages are by weight and all solvent mixture proportions are by volume unless otherwise noted.

EXAMPLE 1

Microsphere Production: Suspension Polymerization Technique

Crosslinked polymer gels (hydrogels) that possess either weakly acidic or basic pendant groups will expand in a solvent, dependent on the pH and ionic composition of the solution. Acidic groups cause the gel to expand as the pH of the solution increases, whereas basic groups result in an expansion as the pH decreases. It has been found that for hydrophobic gels in an aqueous environment, the gel will remain in a collapsed state until the pH reaches a critical value upon which the process of gel ionization is initiated causing an abrupt increase in equilibrium swelling. The equilibrium swelling of these types of polymer gel networks is determined by a balance of the following three forces: 1) the free energy of mixing associated with the polymer gel matrix and the solvent, 2) the net osmotic pressure within the matrix due to the mobile counter ions in the solvent surrounding the fixed charged groups of the polymer gel, and 3) the elastic response of the polymer matrix (Siegel et al., 1988). Some examples of pH sensitive gel materials include cellulose (Grignon et al., 1980), poly(acrylamide-co-acrylic acid) (Peppas et al., 1991), poly(styrene-co-vinyl pyridine) (Batich et al., 1993), and poly(n-alkyl methacrylate-co-diethylaminoethyl methacrylate) (Siegel et al., 1988). The gel matrix is usually composed of a copolymer containing a hydrophobic component and a less hydrophobic ionizable component which are then lightly crosslinked.

Spherical copolymer microspheres were produced using a suspension polymerization technique. A stabilizer solution was first made using 5 g hydroxyethyl cellulose (Aldrich), 1.25 g bentonite (Fisher Scientific), 100 g NaCl (Aldrich), and roughly 525 ml distilled water. The solution was stirred at 60–70° C. for one hour and then filtered through a 53 µm sieve (Fisher Scientific) into a reaction vessel fitted with a mechanical stirrer (RW 20 DZM Janke & Kunkei Ika-Werk, Germany). The monomer solution (60 g total) was prepared by mixing different ratios of ethyl methacrylate (EMA)/ (diethyl amino)ethyl methacrylate (DEA)/divinyl benzene (DVB) (Aldrich/Aldrich/Monomer-Polymer Laboratories) with 250 mg of recrystallized AIBN (Aldrich) (0.4 wt % by monomer). The monomers were vacuum distilled and the divinylbenzene was washed with a 10% sodium hydroxide aqueous solution prior to use. Argon was bubbled through the monomer solution for 1–2 minutes prior to the solution being added to the reaction mixture. The complete reaction solution was stirred at 900 rpm for the entire process. The heating profile was carried out using a heating band around the reaction vessel that was controlled using a Honeywell IACD (mini-pro) temperature profile controller. The temperature profile was as follows: 1) 45 minute ramp from 30 to 75° C., 2) hold at 75° C. for 30 minutes, 3) 30 minute ramp from 75 to 85° C., 4) hold for 4 hours at 85° C. then shut off. After cooling to room temperature the reaction vessel was disassembled and the contents were poured into a 2 liter graduated cylinder that was then topped off with water. The microspheres were initially cleaned by a process of repeated sedimentation and then re-suspension in water over the period of a week. The washed spheres were collected, rinsed with methanol (Fisher Scientific), dried in a paper cone filter (Whatman) for 12 hours, and then placed in a vacuum oven (Napco, E-Series Model 5831) at 60° C. for an additional 12 hours to remove all water and methanol. The dried spheres were broken up with a spatula and sieved to obtain samples with diameters of less than 35 µm, 35–50 µm, 50–80 µm, and 80–150 µm. A total of four trial compositions were produced with 67/30/3, 65/34/1, 60/38.5/1.5, and 50/49/1 mole percent ratios of EMA/DEA/DVB.

EXAMPLE 2

Microsphere Loading and Release of Dye

All four compositions produced in Example 1 were tested for release properties using 9-aminoacridine (Aldrich) (free from HCl) as a test dye. A 100–150 mg sample of each composition (from the 50–80 µm size group) was first washed twice with methanol, allowed to dry, and then immersed in a saturated solution of 9-aminoacridine in methanol (10 wt %) for 24 hours. The methanol was allowed to evaporate (usually for 24 hours) and the microspheres were washed by a repeated process of suspension and centrifuging (Adams Dynac centrifuge) in fresh neutral pH water (at least 10 cycles). The loaded spheres were collected in a paper filter cone and dried in an oven at 60° C. under vacuum.

For each composition, 5 mg of dye-loaded spheres were placed in glass vials (Fisher 20 ml scintillation vials) containing 15 ml of citric acid buffer (0.05 M, I=0.3) at pH 6.0, 6.5, and 6.8. The buffer solutions consisted of citric acid (anhydrous, Fisher Scientific), NaOH (Fisher Scientific), deionized water, and NaCl (Aldrich). A total of three samples were used from each composition at each pH value to account for error involved with the weighing of the microspheres. At least five samples (5 ml each) were taken from each vial over a 14 day period and the concentration of dye released was determined spectrophotometrically at 400 nm using a Perkin-Elmer Lambda 3B UV/VIS spectrophotometer. Each sample was replaced with fresh buffer solution. A 5 mg sample of each composition was also placed into 15 ml of pH 2.5 citric acid buffer (0.05 M) for 24 hours to determine the total percent loading (mg dye released/mg loaded spheres) for the microspheres.

For each microsphere composition, the total percent loading (mg dye/mg microspheres) is shown in the following table:

TABLE 1

| EMA/DEA/DVB | 67/30/3 | 65/34/1 | 60/38.5/1.5 | 50/49/1 |
|---|---|---|---|---|
| Wt % loading | 14.3 | 15.5 | 15.9 | 16.6 |

Figure 2:
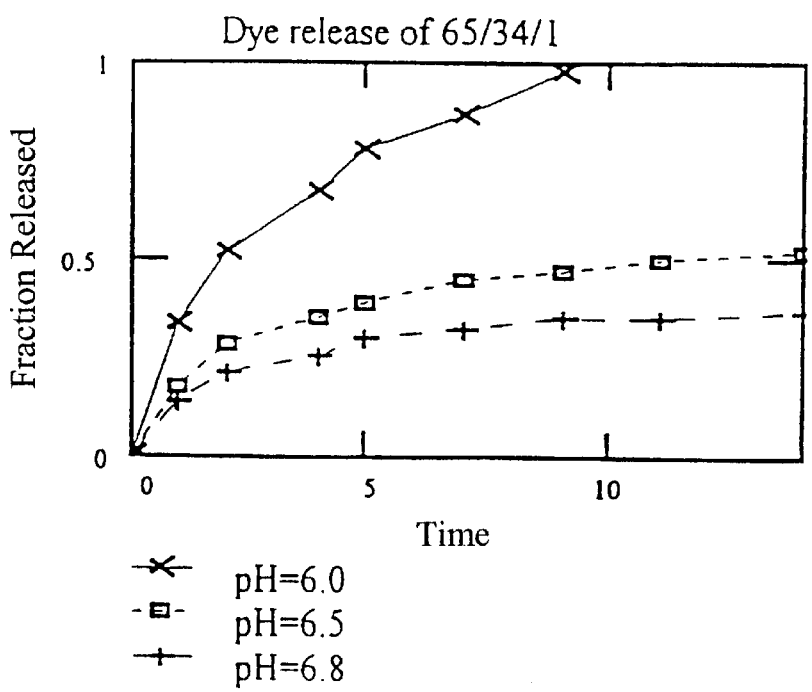
Figure 3:
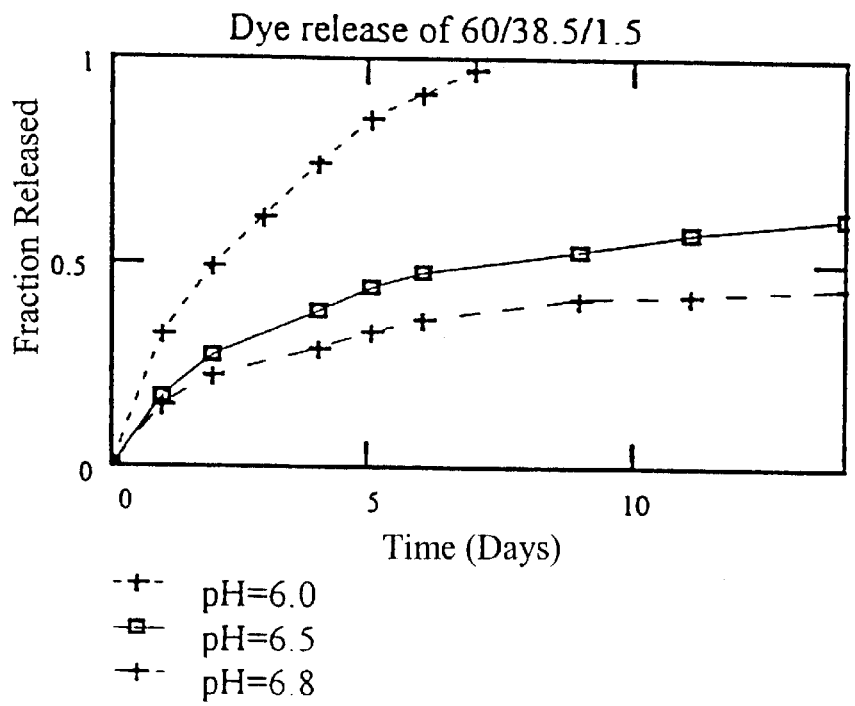

FIGS. 1–3 show the release of the test dye over a 14 day period at pH 6.0, 6.5, and 6.8 for the 67/30/3, 65/34/1, and 60/38.5/1.5 ratios of EMA/DEA/DVB microsphere compositions. In FIG. 1, the microspheres (67/30/3) showed complete release at a pH of 6.0 after 13 days, and less than 50% release at pH 6.5 and 6.8 after the full 14 days. At a pH of 6.8 the spheres showed very little release after an initial burst which may suggest incomplete dye removal from the surface during the cleaning stage. FIGS. 2 and 3 show that by increasing the DEA content (as well as decreasing the amount of crosslinking) of the spheres, an increase in the overall release kinetics results. For the 60/38.5/1.5 composition at a pH of 6.8 there is still less than 50% of the dye released during the desired two week period.

Figure 4:
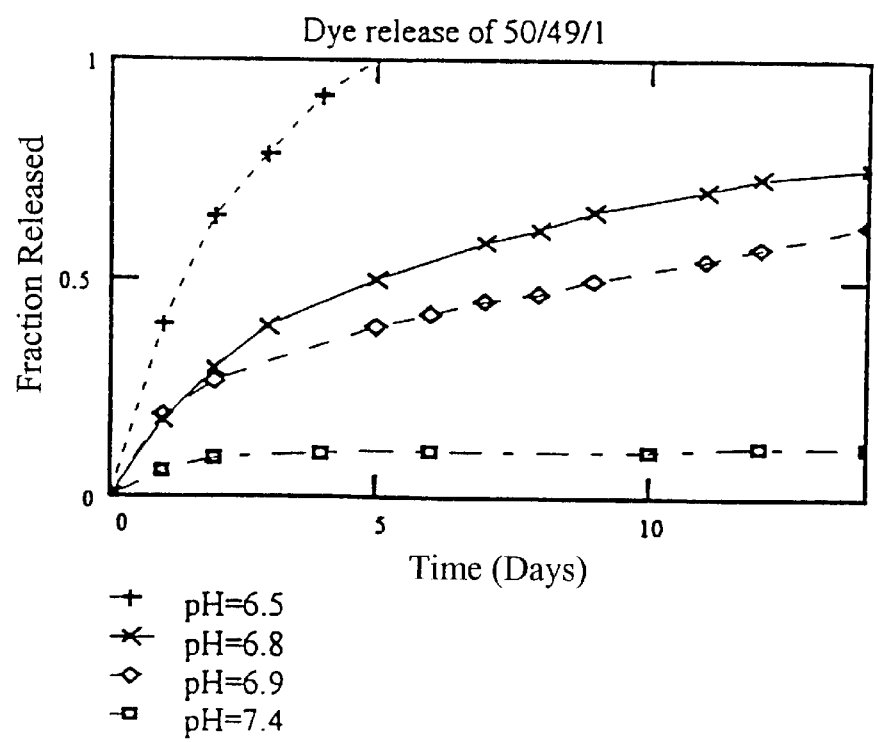
FIG. 4 shows dye release for the 50/49/1 composition at pH's of 6.5, 6.8, 6.9, and 7.4.

FIG. 4 shows dye release for the 50/49/1 composition at pH's of 6.5, 6.8, 6.9, and 7.4. At a pH of 6.0 complete release was achieved over a period of several hours. At pH 6.8 and pH 6.9 about 76% and 63%, respectively, of the dye was released over the 14 day period. The experiment at pH 7.4 was done using a potassium phosphate monobasic-NaOH buffer (0.05 M) (Fisher Scientific) to ensure that release was minimized at a normal biological pH range. At this pH, roughly 14% of the dye was released after two weeks. This release may be due to incomplete surface cleaning or to release from a shallow surface layer with a short diffusion distance. Since the two week release range of this 50/49/1 composition was near 6.7, it was chosen as the composition used for the in-vitro drug release experiments.

EXAMPLE 3

In Vitro Drug Release

During preparation for in vivo experiments it was determined that in order to inject the microspheres into the hepatic artery of a rat, a very fine (26 gauge) needle was required Preliminary experiments showed that the 50–80 µm diameter microspheres tended to clog the needle in a significant percentage of initial trials. Since this was much less of a problem for microspheres with diameters smaller than 50 µm a second set of release experiments was designed to determine what, if any, effect different size ranges (35–50 µm and 80–150 µm) have on the loading and release characteristics of the spheres.

The in vitro drug release experiments were done using the chemotherapeutic drugs fluorodeoxyuridine (FUDR) (Sigma) and doxorubicin (hydroxydaunomycin hydrochloride) (Sigma). Due to the high cost and small quantities available for these two test drugs, the solutions used for loading the microspheres were limited to 5 mg/ml in methanol.

Initial FUDR Test. 150 mg of 50–80 μm diameter EMA/DEA/DVB (in a ratio of 50/49/1) microspheres were washed twice with methanol, dried and then immersed in 1 ml of methanol containing 5 mg FUDR. After 24 hours the methanol was allowed to evaporate and the loaded spheres were dispersed in 50 ml of distilled water and centrifuged repeatedly for 10 cycles. The spheres were collected and allowed to dry in a cone filter under the hood for 24 hours. 10 mg of the loaded spheres were placed in each of two separate vials containing either 15 ml of pH 6.8 citric acid buffer (0.05 M I=0.3) or pH 7.4 potassium phosphate monobasic-NaOH buffer (0.05 M, Fisher Scientific). Each vial was agitated by hand daily and a total of 5 samples (5 ml each) were taken over a 14 day period and measured spectrophotometrically at 268 nm to determine the FUDR concentration in solution. Each sample was replaced using fresh buffer. The total percent loading was determined by the same process after placing a 10 mg sample of spheres into 15 ml of pH 4.0 citric acid buffer for 24 hours.

Follow-up FUDR Release. After the initial FUDR release experiment showed that the drug release was sufficient for measurement, the remainder of the FUDR release experiment was carried out as described in Example 2 using citric acid buffer pH values of 6.6 and 6.9 with a total of three repetitions for each. Sample volumes of 5 ml and 3 ml were taken from the pH 6.6 and 6.9 buffers, respectively.

Doxorubicin Release. The doxorubicin release experiments were carried out in the same manner as the FUDR and dye release. 150 mg of 50–80 μm diameter microspheres were cleaned and immersed in 1 ml of methanol containing 5 mg of the drug for 24 hours and the methanol was allowed to evaporate slowly under the hood. The loaded microspheres were cleaned and dried and 10 mg samples were placed into 20 ml glass vials (Fisher Scientific). 15 ml of citric acid buffer was placed into each vial such that there were three samples each at pH values of 6.6, 6.75, and 6.9. Drug release at pH 7.4 was performed using 15 ml potassium phosphate buffer added to each of the remaining three vials. Drug release was measured spectrophotometrically at 479 nm.

Size Related Dye Release. 100 mg samples of 35–50, 50–80, and 80–150 μm diameter EMA/DEA/DVB (50/49/1) microspheres were cleaned and loaded with 9-aminoacridine using the same procedure described in Example 2. Release was carried out using 5 mg samples of spheres immersed in 15 ml of pH 6.5 and 6.7 citric acid buffer solutions for 14 days. A total of three repetitions were done for each size range at each pH. Solution dye concentrations were measured spectrophotometrically at 400 nm.

Dosages. FUDR (fluorodeoxyuridine) is commonly administered to patients with primary or secondary liver carcinomas by continuous regional infusion. Most of the drug appears to be anabolized to FUDR-monophosphate, the active metabolite of the drug which inhibits thymidylate synthetase thereby interfering with the synthesis of DNA. When doses are administered rapidly, FUDR is catabolized to fluorouracil which has similar effects as FUDR and metabolites of which interrupt normal RNA production (Budavari et al., 1989). Both FUDR and fluorouracil are metabolized in the liver, but this is somewhat reduced when the drug is given by continuous infusion rather than single injections. A standard FUDR dose given to human patients by hepatic arterial infusion is about 0.1 to 0.6 mg/Kg/day (Trissel, 1994) while the dose given to the rat model used by Ward et al. (1992) was either 1 mg/Kg/day systemically or 2 mg/Kg/day regionally for 7 days. If the microspheres were loaded at 14 weight percent (mg drug/mg spheres) with FUDR, there would be enough drug within 50 mg of the spheres to release this same 2 mg/Kg/day for 14 days within a typical 250 gram rat. For a tumor burden estimated at about 10% of the liver mass at treatment stage, this works out to be around 0.7 mg of FUDR released specifically within the tumor tissue with the remaining 90% trapped in the microspheres or released at very low, non-cytotoxic levels within the healthy liver areas. However, since it is known that preferential hepatic angiogenesis of tumor tissue should deliver more particles to the tumor (Meade et al., 1987), this is actually a worst case scenario.

Due to the high cost of the FUDR, a saturated loading solution to determine the true percent loading of the spheres was not prepared. The 5 mg/ml solution resulted in a loading level of only 1.4 weight percentage of loading. However, since 500 mg samples of FUDR are commonly constituted in 5 ml sterile water (100 mg/ml), it may be assumed that the drug solubility is such that high loading levels can be obtained. For comparison, 100 mg of 9-aminoacridine dye per ml of methanol were used earlier to load about 15% of dye.

Figure 5:
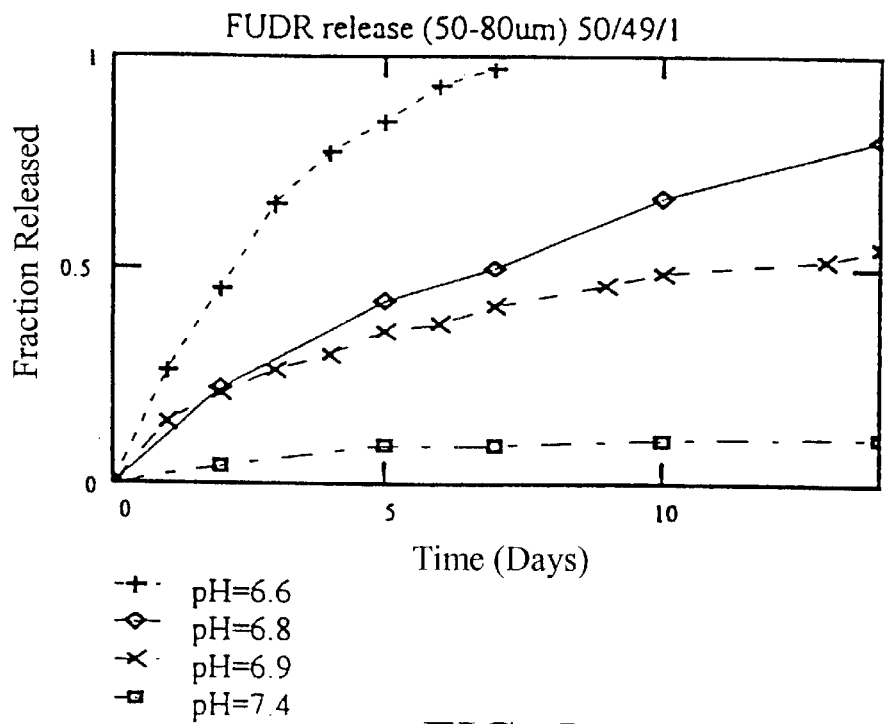
FIG. 5 shows the release curves for the FUDR in buffer at 4 different pH values.

FIG. 5 shows the release curves for the FUDR in buffer at four different pH values. At pH 6.8 the spheres had released 80% of the encapsulated drug over the 14 day period as compared to a 76% release of the test dye under the same conditions. At pH 6.9 the 14 day release values for FUDR and the dye were 55% and 63%, respectively. In both cases, just over 10% of the microsphere contents were released when exposed to pH 7.4. The release rate and the total fraction of released contents seem to compare well for both the dye and FUDR loaded spheres despite the fact that the FUDR was loaded into the spheres under relatively dilute conditions.

Doxorubicin (hydroxydaunomycin hydrochloride) is commercially available as the hydrochloride salt. It is an antineoplastic antibiotic but it is too cytotoxic to be used as an anti-infective agent. The exact mechanism of its anticancer activity is not well understood but some evidence suggests that the drug forms a complex with DNA which inhibits both DNA synthesis and DNA-dependent RNA synthesis by the resulting template disordering. Cells that are the most sensitive to doxorubicin are from rapidly proliferating tissues such as those of normal bone marrow, gastrointestinal mucosa, and hair follicles (Budavari, et al., 1989). Doxorubicin is administered intravenously and commonly used in the treatment of solid tumors including bladder carcinoma, breast carcinoma, ovarian carcinoma, gastric carcinoma, malignant lymphomas, and acute lymphoblastic and myeloblastic leukemias. Doxorubicin is rapidly metabolized in a first pass effect through the liver by an aldo-keto reductase enzyme which forms doxorubicinol, the metabolite with the major antineoplastic activity. The resulting plasma concentrations of doxorubicin and its metabolites are prolonged due to absorption by cells and binding to cellular components such as nucleic acids (Trissel, 1994). The plasma half life concentrations of doxorubicin and its metabolites is 16.7 and 31.7 hours, respectively, and can be longer in patients with impaired hepatic function. The drug is primarily excreted in bile and in feces with only 4–5% excreted in urine. The use of doxorubicin for liver cancer treatment has for the most part been limited to hepatocellular carcinoma; however, it has produced clinically important responses in combination with other chemotherapeutic agents and/or surgery in the early stages of this form of the disease (Budavari, et al., 1989). A common adult dose of doxorubicin would be a 60 to 75 mg/m$^2$ (skin area), intravenous injection once every 21 days, but other schedules require smaller injections (20–30 mg/m$^2$) either once weekly or for 3 to 4 successive days every few weeks (Trissel, 1994).

Figure 6:
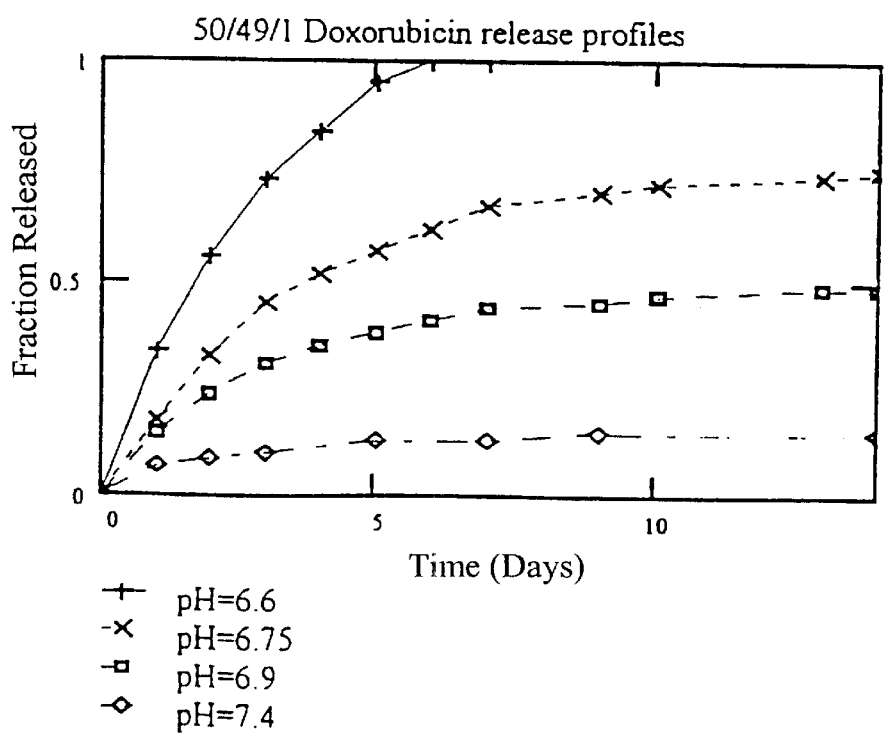
FIG. 6 shows doxorubicin release from 50/49/1 EMA/DEA/DVB microspheres.

FIG. 6 shows the release profiles for doxorubicin in citric acid buffer at 4 different pH values. At pH 6.75 the spheres release 75% of the drug over the two week period which is close to the 80% release obtained for the FUDR at pH 6.8. Neither of the drugs nor the test dye show more than 80% release over a pH of 6.75 during the 14 day period. However, all three show complete release in under one week at a pH of 6.5 to 6.6. This indicates that the microspheres have a relatively sharp swelling transition. Under in vivo conditions where the tumor pH is higher than 6.7, the clinician can administer glucose to achieve a lower intratumoral pH or use a suitable microsphere composition of the present invention that has a swelling transition to release loaded substances at a higher pH level.

Figure 7:
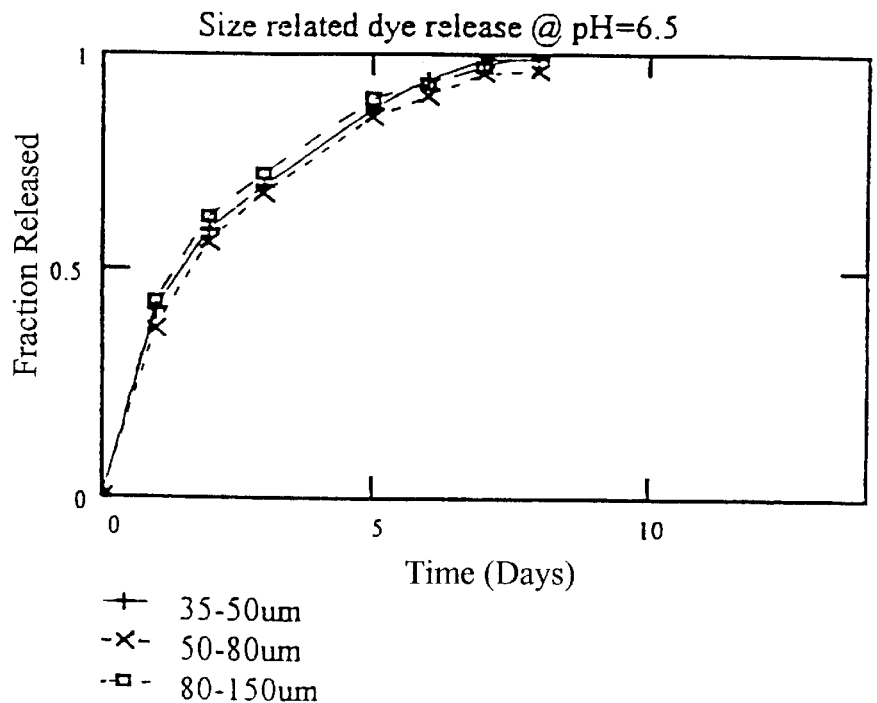
FIGS. 7 and 8 show release profiles for three different size microsphere samples at two different pH values.
Figure 8:
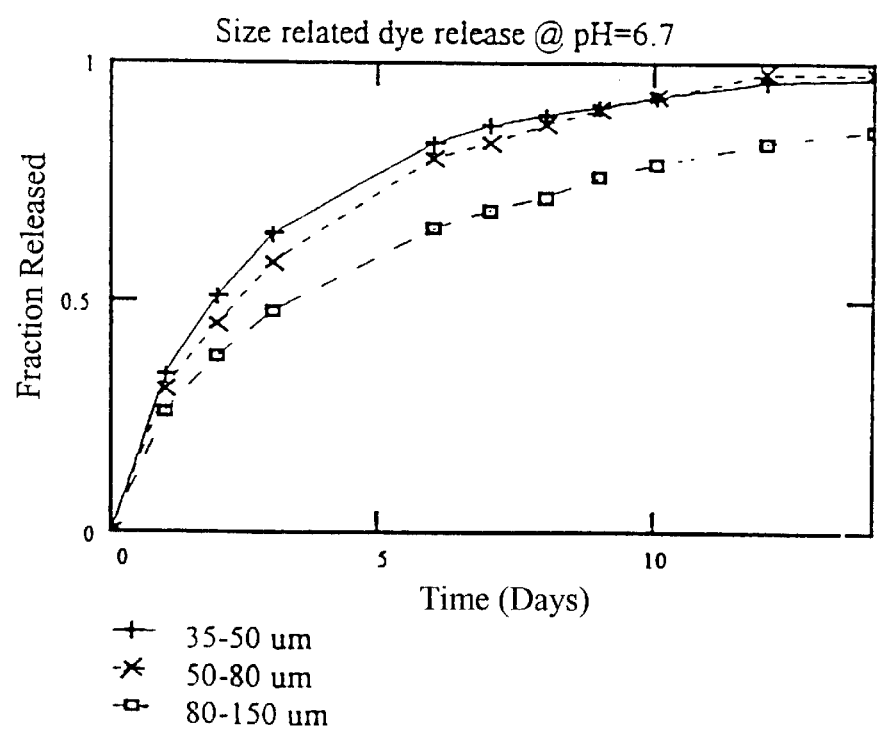

FIGS. 7 and 8 show release profiles for three different size microsphere samples at two different pH values. In FIG. 7 the curves virtually overlap which shows that at pH 6.5 the microsphere swelling is such that the dye release has little or no dependence on the sphere size. However, in FIG. 8, which shows release at pH 6.7, the 80–150 μm diameter spheres show a noticeably slower release with a 14 day total of only 86% compared to 98% for the smaller spheres. The smaller spheres have more surface area in contact with the buffer solution as well as shorter diffusion distances which most likely explains the faster release. At pH 6.7, which is relatively close to the swelling transition for this particular microsphere composition, the release rate is slow enough that this effect can be seen. However, as the pH becomes more acidic, the microspheres release quickly enough that the difference can no longer be seen. At pH 6.7 there is virtually no difference between the release profiles of the 50–80 μm and 35–50 μm diameter spheres, but as the pH increases to 6.8–7.0 it is possible that the smaller spheres may show a slightly faster release rate.

EXAMPLE 4

In Vivo Compatibility

Empty Microsphere Injection. 200 mg of 50–80 μm diameter EMA/DEA/DVB (50/49/1) microspheres were washed by stirring in ethanol for 12 hours and then dried under the hood before in vivo injection. The animals used in this study were BD-IX rats weighing 150–250 grams (7–8 weeks old). All surgical procedures were performed under general anesthesia with phenobarbital injected intraperitoneally using 60 mg/Kg (body weight).

A midline incision was made in a rat, and with the aid of an operating microscope the hepatic artery was isolated and ligated distally with a 6-0 silk tie. This, along with a second loop placed proximally, was used to control bleeding during the injection procedure. A few drops of lidocaine were applied to the artery to prevent spasms during the procedure. A small incision was made in the artery using micro dissection scissors and a catheter made from Biolab (0.023 inch inner dia.) vinyl tubing was inserted into the artery and secured by a silk tie. A 25 gauge syringe needle was inserted into the catheter and a suspension (1 ml) made from 50 mg of the microspheres in a 50% glycerol aqueous solution was ultrasonicated for roughly one minute to break up any microsphere aggregates and then slowly injected into the artery over a 30 second period. Finally, 5 ml of sterile saline and 100,000 units of penicillin were injected into the peritoneal cavity and the incision was closed using a 4-0 silk suture. The skin was closed with 9-mm stainless steel autoclips and the rat was allowed to recover under warming lights.

Histology Slide Preparation. After 24 hours the rat was sacrificed and the liver was harvested and fixed in 3% buffered formalin. The liver was then embedded in paraffin and cut into 5 μm sections using a microtome. The sections were placed on slides and the paraffin was removed using acetone. The sections were finally re-hydrated with several alcohol/water solutions with increasing water content. In order to promote microsphere visibility in the slides, the spheres were washed with eosin (a basophilic stain) prior to the injection procedure.

Dye Loading and Injection. 500 mg of 50–80 μm diameter EMA/DEA/DVB (50/49/1) microspheres were cleaned by stirring in 40 ml ethanol for 12 hours before being collected and dried under the hood. The spheres were placed into 3 ml of methanol containing 10 wt % 9-aminoacridine for 24 hours. The loaded spheres were washed by 10 cycles of shaking in 50 ml of distilled water and then collected by centrifuging. The spheres were then dried and separated using a spatula. The surgical procedure was basically the same as described previously except that it was performed on two separate rats which each received 150 mg of the microspheres injected directly into the portal vein through a 23 gauge needle without the use of a catheter. Rats were sacrificed immediately after injection and their livers were removed and frozen.

Microsphere Retrieval. The removed rat livers were thawed and cut into small cubes roughly 1 cm wide. Each liver was put into 100 ml of a 2M potassium hydroxide (Fisher Scientific) solution and stirred magnetically for 24 hours on low heat (45–50° C.). At this point the liver tissue was completely dissolved and the contents of each beaker was poured 25 ml at a time into a 50 ml centrifuge tube (Fisher Scientific) with 25 ml of distilled water. Each tube was centrifuged for 5 minutes and the supernate was removed. This was repeated until all of the dissolved liver solution had been used. The microspheres that were collected were washed twice with water, dried in a paper cone filter (12.5 cm Whatman filter paper) under the hood, and then weighed. Two 5 mg microsphere samples from each liver were placed into 15 ml of pH 4 citric acid buffer solution for 24 hours. Also two 5 mg samples were taken from the remaining microspheres that were not injected, and placed into 15 ml of pH 4 citric acid buffer for 24 hours to serve as a control group. The total dye release for each sample was measured at 400 nm by UV/VIS spectrophotometry.

Results—Dye Loaded Microsphere Retrieval. Because of the problems associated with the hepatic arterial injection of the microspheres, the portal vein was chosen in this experiment due to its larger size. This enabled the use of a larger needle (23 gauge) without the catheter which greatly reduced the chances of being blocked and allowed for a larger injection volume of spheres (150 mg).

After 24 hours in a 2M potassium hydroxide solution the liver tissue was dissolved leaving only some cellular debris remaining. Upon centrifuging, the microspheres, which are more dense than water, formed the bottom layer in the centrifuge tube. The majority of the cellular debris remained suspended in solution, but there was a thin layer on top of the microspheres that had to be removed with a glass pipette (Fisher Scientific). A total of 77 mg and 91 mg of microspheres were removed from each of the two livers which were originally injected with 150 mg. Although some of the microspheres may have passed through the liver during the injection process due to the broad size distribution, the majority of microspheres were most likely lost during the collection process. Some of this probably could have been avoided if volumes larger than 25 ml of the solution were centrifuged at a time because each time the layers of debris were removed a small quantity of spheres were lost.

The loading percentages for the spheres collected from the livers were 15.3% and 14.9% (weight of dye/weight of spheres) compared to the control group which was loaded at 16.2%. Since the potassium hydroxide solution is basic it is unlikely that dye was released during the tissue dissolution process. A trial experiment also showed that the spheres do not release in a 50% glycerol aqueous solution. However, during the sonication process it seems possible that any dye left on the surface after washing could have been removed. The spheres were in living tissue for only a short time (10–15 minutes) before being frozen so any release during that time should be at a minimum. One possible reason for some dye release would be the two final washings with distilled water which does have a pH of less than 7.0. Washings of the loaded spheres should be done in a sodium hydroxide aqueous solution to reduce this effect. It is also possible that a small percentage of the microsphere sample that was weighed after the procedure was actually left over cellular debris that was not completely removed during the collection and washing of the spheres. Since this would result in a smaller quantity of spheres in the sample, less release would be expected. Overall, this experiment showed that for a portal vein injection of microspheres, over 50% of the injected spheres could be retrieved from the liver with at least 90% of their contents still intact. The collection procedure would be more difficult for a hepatic arterial injection because of both the smaller size and quantity of the microspheres used; however, the use of smaller, more monodisperse microspheres should be effective.

EXAMPLE 5

Microsphere Size Control and Production of Microspheres—Dispersion Polymerization and Activated Swelling Dispersion Polymerization. The dispersion polymerization experiments were done using 25 ml glass vials with screw on caps (Fisher Scientific) placed horizontally in a constant temperature shaker bath (Blue M, Magni Whirl) set at 55° C. The standard components for each reaction were methanol, poly(vinyl pyrrolidone) (PVP 40, 40,000 MW, Sigma), AIBN(re-crystallized in methanol), ethyl methacrylate, Diethyl(aminoethyl methacrylate), divinyl benzene, and ethylene glycol dimethacrylate (Aldrich). All of the following percentages are given in weight percent according to a total 10 gram sample.

The initial recipe for the polymerization reaction was chosen to be 10% monomer (3:2 ratio of DEA:EMA by weight), 3% poly(vinyl pyrrolidone) (PVP), 0.3% AIBN, and 86.7% methanol. The PVP was dissolved in the methanol and then filtered directly into the 25 ml reaction vial using a 0.45 µm pore size (Whatman) syringe filter attached to a 10 cc syringe (Becton-Dickinson). The AIBN was dissolved into the monomer which was then mixed into the reaction solution by vortexing for 1 minute. Nitrogen or argon gas was bubbled through the reaction solution for at least 2 minutes and the reaction vial was capped, sealed with PARAFILM (American National Can), and placed horizontally into the shaker bath at 55° C. for 24 hours. This reaction was repeated 3 additional times replacing the 86.7% solvent portion with water/methanol ratios of 15/85, 30/0, and 40/60. After each reaction was completed the solution was poured into 100 ml of water and stirred magnetically for 1 hour, at which point the microspheres were collected by centrifuging and dried in a paper filter.

In order to determine the effect of initiator concentration on the microsphere size, additional reactions were done using 0.1% and 0.4% AIBN. Both reaction solutions contained 10% monomer and 3% PVP with the remainder of the 10 gram total comprised of distilled water and methanol (30/70 wt %). The reactions were carried out under the same conditions.

The amount of PVP stabilizer was changed in two reactions to 1% and 5% with a constant initiator concentration of 0.3%. The monomer concentration and the water/methanol ratio remained at 10% and 30/70, respectively. The reactions were carried out under the same conditions.

Three additional reactions were carried out using monomer concentrations of 5%, 15%, and 20% (3:2 ratio of DEA/EMA by weight). The concentrations of PVP and AIBN were 3% and 0.3%, respectively, and the water/methanol ratio remained at 30/70. The reaction conditions were the same.

In an attempt to produce crosslinked microspheres, two reactions were carried out using 0.3% and 0.6% (based on monomer weight) of ethylene glycol dimethacrylate. The other variables were 15% monomer, 0.3% AIBN, 3% PVP, and the remainder distilled water and methanol in a 30/70 ratio.

Activated Swelling Method. In the first step (pre-swelling) of this procedure 25 mg of monodisperse 2–3 µm diameter poly(ethyl methacrylate) (PEMA) microspheres were sonicated (Sonica & Materials, Inc., Vibra Cell) for 30 seconds in 3 ml of distilled water in a 5 ml test tube (Fisher Scientific) to disperse the spheres in solution. This was added to an emulsion of 10 ml distilled water, 30 mg sodium dodecylsulfate (SDS) (Sigma), and 125 mg of dibutyl phthalate (Fisher Scientific) which was sonicated again for 1–2 minutes. The entire solution was put into a 50 ml round bottom flask and was stirred magnetically for 24 hours. In the second step another emulsion consisting of 10 ml distilled water, 2 grams monomer (3:2 ratio of DEA/EMA by weight), 20 mg divinyl benzene (crosslinking monomer), 20 mg SDS, 200 mg PVP, and 30 mg each of the co-initiators ethyl 4-dimethylaminobenzoate (Acros) and d1-camphoroquinone (Acros) was sonicated for 1–2 minutes and added to the solution of swollen spheres produced in the first step. The solution was purged with nitrogen for 5 minutes while being magnetically stirred at slow speed. Once the microspheres became swollen with monomer (usually about 1 hour) a variable light source was turned on using a 140 volt Staco Energy Products Co. Variable Autotransformer (set at 50%) and placed roughly 8 inches from the round bottom solution flask. After 2 hours the light source was removed and the solution was stirred for an additional 24 hours. The reaction contents were poured into a 200 ml beaker containing 100 ml of warm isopropanol (LabChem, Inc.) and stirred for 2 hours before collecting the microspheres by centrifuging in 50 ml centrifuge tubes.

Results. The variables which are involved in determining the particle size distribution for a typical suspension polymerization process include stirring speed, the volume ratio of the monomer to suspension medium, stabilizer concentration, and the viscosity of both phases. The mechanical homogenization step produces an inherent size particle distribution which is typically anywhere from 20 µm to 2 mm in diameter (Arshady, 1992). Procedures such as wet sedimentation, counter flow settling, and counter flow centrifugation can be used for the size separation and classification but these methods are relatively difficult to implement and the reliability can be relatively poor (Hosoya et al., 1993). The microspheres produced in this research were separated into size groups using metal sieves having different size openings. Attempts were made to separate out a 10–20 μm diameter sample using 10 and 20 μm spectra fiber woven meshes, but there was just not enough microspheres within this range produced by the suspension method. Emulsion polymerization techniques are commonly used to produce monodisperse particles, however they are typically in the nanometer size range which is far too small for use in this study (Arshady, 1992).

The dispersion polymerization process has become increasingly important, not only because it allows for the production of monodisperse microspheres within the micron range (2–20 μm), but also because of the simplicity of the process and the wide variety of monomers that can be polymerized (Arshady, 1992, Shen S., 1993). Generally, the particle sizes produced using this technique range from 1–10 μm in diameter. However, by manipulating the reaction variables (Lok et al., 1985) produced monodisperse polystyrene spheres 12 μm in diameter (Arshady, 1992). The dispersion polymerization reaction starts out as a homogeneous solution consisting of monomer, solvent, initiator, and stabilizer in which the medium is miscible with the monomer but not the polymer. As the initiator decomposes free radicals form and grow in the continuous phase until they reach a critical chain length where they precipitate out and form nuclei. The nuclei are unstable and absorb the polymeric stabilizer chains while aggregating with each other until enough stabilizer is absorbed forming mature particles. This particle formation stage continues until there are enough mature particles formed to capture all the radicals and nuclei in the continuous phase (Shen S., 1993). The mature particles then capture oligo-radicals and nuclei which will continue to grow inside the particles or terminate with other radicals. At the end of the polymerization reaction the nuclei formation stops due to either lack of monomer or radicals. To form monodisperse particles the reaction must have a short particle formation stage (compared to the growth stage) and a growth stage that is free from the formation of new particles and the coalescence of existing particles (Shen et al., 1994).

Initial experiments designed to produce monodisperse microspheres of the correct 50/49/1 EMA/DEA/DVB copolymer using dispersion polymerization techniques were done using methanol for a solvent, AIBN as the initiator, and PVP as the stabilizer. The concentrations of 86.7%, 0.3%, and 3.0% (based on a 10 gram total including 10% monomer) respectively were chosen based on previous studies using poly(methyl methacrylate) (Shen S. et al., 1993, Bulmus et al., 1996). However, in this study it was shown that the copolymer that was formed during the polymerization reaction remained soluble until the solvent portion of the reaction (86.7%) included at least 30% distilled water (70% methanol). The spheres produced from this recipe are reasonably monodisperse with the average diameter around 4 μm which was determined by optical microscopy (using graduated eyepiece) and verified by a scanning electron microscope (SEM). As the percentage of water in the solvent portion of the reaction was increased to 40%, the average size of the microspheres decreased (1–2 μm dia.) but remained monodisperse. As the water content is increased, the polymer formed is less soluble and tends to precipitate out at lower molecular weights, which produces more nuclei in the particle formation stage, resulting in smaller particles (Tuncel et al., 1994). Therefore, in this study the lowest water/methanol ratio that allowed polymer to precipitate (30/70) was used for the remainder of the experiments.

In the next set of experiments the initiator concentration was varied from 0.1% to 0.4% with the other variables constant. As the concentration was increased, the size and polydispersity of the spheres increase as well. These results were similar to those obtained by Shen S. et al. (1993) for poly(methyl methacrylate) (PMMA) microspheres which increased in size from 3 to 8 μm in diameter over the same range of initiator concentration. They determined that by increasing the initiator concentration, the radical concentration increases, which leads to the formation of lower molecular weight chains that are more soluble in the reaction medium. Since the higher molecular weight chains precipitate to form nuclei, there ends up being a smaller number of mature particles formed which grow to be a larger size. However, since this also affects the length of the particle formation stage of the reaction, there exists a maximum concentration of initiator for producing monodisperse particles under given conditions. The microspheres produced using 0.3% AIBN were considerably more monodisperse than those produced using 0.4%, so the 0.3% concentration was used in the remainder of the experiments.

Shen et al. (1994) showed that both the stabilizer concentration and molecular weight had an effect on the final size of particles produced by dispersion polymerization. They concluded that an increase in the stabilizer concentration or molecular weight increases the viscosity of the medium, as well as the physical rate of stabilizer adsorption which both have the effect of reducing the extent of nuclei aggregation, resulting in an overall decrease in particle size. However, in this study as the PVP concentration was varied from 1–5%, the change in microsphere size was minimal and the sample with a 5% concentration showed an increase in size distribution very similar to that seen for the increasing initiator concentration. The only molecular weight of the PVP available for use in these experiments was 40,000 which was at the low end of what was used in the study by Shen et al. (1994). The low molecular weight may account for the minimal effect of the concentration on the particle size, but this was not shown to be the case in other studies (Shen et al., 1994, Bulmus et al., 1996).

All of the previous experiments were done using 10% monomer in the polymerization recipe. In order to determine the effect of monomer concentration on particle size, a series of experiments were done using 5%, 15%, and 20% monomer, with the other variables at their optimum value. The batch with 5% monomer produced monodisperse microspheres, but as expected their average size was smaller than those produced in previous experiments. The 15% monomer sample was larger (5 μm average dia.) but the distribution became somewhat broader. A further increase in monomer concentration to 20% only increased the size distribution with no noticeable particle size increase. These results generally agree with those obtained by Shen S. et al. (1993) who determined that increasing the monomer concentration increases both the initial solvency of the medium and the length of the particle growth stage which both act to increase the overall particle size. Therefore, it was determined that for this copolymer system the optimum values for the dispersion polymerization variables were 0.3% initiator, 3.0% stabilizer, 10–15% monomer, and the remainder solvent (water/methanol 30/70 ratio).

Since the maximum monodisperse particle size that could be obtained by this method was roughly 4 to 5 µm in diameter, several techniques were attempted in an effort to grow these particles to within the desired 10–15 µm range. These "seeded polymerization" methods failed due to dissolution or aggregation of the particles caused by the monomer added to the system. Efforts to overcome the dissolution problem by crosslinking the particles during the dispersion polymerization process were also unsuccessful because even low concentrations (0.3–0.6 wt % based on monomer) caused severe particle flocculation.

The activated swelling principle was first demonstrated by Ugelstad et al. (1980) and has become the only method available which allows preparation of extremely monodisperse, crosslinked particles within the micron range (2–20 µm) (Christensen et al, 1996). Typically, it is difficult to swell polymer particles with monomer because the particles usually only absorb 1–10 times their own volume. Therefore, a seeded polymerization process may require multiple swelling and polymerization steps in order to double the diameter of the original seed particles which would increase the volume by a factor of 8. Since each step increases the chances of secondary particle formation and particle agglomeration, this process can prove to be unreliable (Ugelstad et al., 1980). In the first step of the activated swelling method, a "swelling agent" consisting of a highly water insoluble compound of relatively low molecular weight is introduced into the monodisperse particles (1:1 to 1:5 volume ratio) in the form of an emulsion. Once the particles are completely swollen, a second emulsion is added containing the slightly water soluble vinyl and divinyl monomers (and initiator). The "activated" particles may absorb from 100 to more than 1000 times their own volume of the compounds added in this second step. The swollen particles can then be polymerized by increasing the temperature of the reaction. Since all of the ingredients are introduced into the particles before polymerization, the result is a high degree of monodispersity and batch reproducibility (Ugelstad et al., 1980).

Dibutyl phthalate was used as a swelling agent in this study to swell highly monodisperse (2–3 µm dia.) poly(ethyl methacrylate) microspheres produced by dispersion polymerization techniques. PEMA microspheres were used as seed particles because of the high degree of particle uniformity obtainable for that system. The comonomers, including divinyl benzene as a crosslinking agent, were added in the second step but due to the degree of water solubility of the DEA monomer, the swollen particles only remained stable for roughly 2 hours. By increasing the temperature to carry out the polymerization, the kinetics of the swollen droplet degradation increased and very non-uniform particles were produced. However, this problem was overcome by substituting a photoinitiator system composed of ethyl 4-dimethylaminobenzoate and d1-camphoroquinone for the AIBN. Since this system resulted in room temperature polymerization within an hour, the swollen particles produced in step 2 of the activated swelling method could be polymerized in time to retain their shape and size. The PEMA seed particles account for less than 2% of the final microsphere volume and since the PEMA is soluble in hot isopropanol, most (if not all) of the seed can be removed during the cleaning procedure.

Preliminary loading and release studies using the microspheres produced by this technique showed that they could be swollen in methanol and loaded with the test dye (9-aminoacridine). In three separate experiments, loading levels between 15% and 16% were obtained which is only slightly lower than the 16.6% loaded into the spheres produced by suspension polymerization. A small difference can probably be expected due to both the differences in the microspheres size range and the monomer volumes used in each production technique (60 grams compared to 2 grams). Also, the monodisperse microspheres were produced using twice as much crosslinking content (2%) which decreases the overall loading potential.

It should be understood that the examples and embodiments described herein are for illustrative purposes only and that various modifications or changes in light thereof will be suggested to persons skilled in the art and are to be included within the spirit and purview of this application and the scope of the appended claims.

References

Arshady, R. (1992) "Suspension, emulsion, and dispersion polymerization: A methodological survey," *Colloid & Polymer Science* 270:717–732.

Bhattacharya, S., Novell J. R., Winslet, M. C., Hobbs, K. E. F. (1994) "Iodized oil in the treatment of hepatocellular carcinoma" *Br. J. Surg.* 81:1563–71.

Braun, A. C. (1974) *The Biology of Cancer,* Addison-Wesley Publishing Company.

Budavari, S., Oneil, J. M., Smith, A., Heckelman, P. E., (Eds.) (1989) *The Merck Index: an encyclopedia of chemicals, drugs, and biologicals,* (11$^{th}$ ed.), Merck & Co., Inc.

Bulmus, V., Tuncel, A., Piskin, E. (1996) "Production of polymethylmethacrylate particles by dispersion polymerization in aqueous media with ceric ammonium nitrate," *J. Appl. Polym. Sci.* 60:697–704.

Busch, H., (ed.) (1974) *The Molecular Biology of Cancer.* Academic Press.

Christensen, B. E., Myhr, M. H., Aune, O., Hagen, S., Herge, A., Ugelstad, J. (1996) "Macroporous, monodisperse partiless and their application an aqueous size exclusion chromatography of high molecular weight polysaccharides," *Carbohydrate Polymers* 29:217–223.

Hafeli, U. O., Siobhan, M. S., Bersford, B. A., Sim, E. H., Macklis, R. M. (1994) "Magnetically directed poly(latic acid) Y(90)-microspheres: Novel agents for targeted intracavitary radiotherapy" *J. Biomed. Mat. Res.* 28:901–908.

Hosoya, R., Frechet, J. M. J. (1993) "Influence of the seed polymer on the chromatographic properties of size monodisperse polymeric separation media prepared by a multistep swelling and polymerization method, " *J. Polym. Sci. Part A: Polym. Chem.* 31:2129–2141.

Jahde, E., Ragewsky, M. F. (1982) "Tumor-selective modification of cellular microenvironment in vivo: effect of glucose infusion of the pH in normal and malignant rat tissues" *Cancer Res.* 42:1505–1512.

Kato, T., Nemoto, R., Mori, H., Takahashi, M., Tamakawa, Y., Harada, M. (1981) "Arterial chemoembolization with microencapsulated anticancer drug" *JAMA* 245:1123–1127.

Kemeny, N., Carr, B., Civalleri, D., Hakansson, L., Lindberg, B., Gunnorsson, K., Nilsson, B., Taguchi, T., Khayat, C., Aigner, K. R., (eds) (1995) *An Update on Regional Treatment of Liver Tumours, The Role of Vascular Occlusion,* (Sec. Ed.), Wells Medical Ltd.

Lin, D. Y., Liaw, Y. F., Lee, T. Y., Lai, C. M. (1988) "Heparic arterial embolization in patients with unresectable hepatocellular carcinoma: A randomized controlled trial" *Gastroentereology* 94:453–456.

Lok, K. P., Ober, C. K. (1985) "Particle size control in dispersion polymerization of polystyrene," *Can. J. Chem.* 63:209–216.

Meade, V. M., Burton, M. A., Gray, B. N., Self, G. W. (1987) "Distribution of different sized microspheres in experimental hepatic tumours," *Eur. J. Cancer Clin. Oncol.* 23:37–41.

Muir, B. L., R. N., M. Sc. (1988) *Pathophysiology, An introduction to the Mechanisms of Disease,* John Wiley & Sons.

Narayani, R., Panduranga, K. (1995) "pH-Responsive gelatin microspheres for oral delivery of anticancer drug methotrexate" *J. App. Polym. Sci.* 58:1761–1769.

Oppenheimer, S. B. (1985) *Cancer, A Biological and Clinical Introduction,* second edition, Jones and Bartlett Publishers, Inc.

Shen, C., Rao, P. V., Batich, C. D., Moorhead, J., Yan, J. (1994) "Stochastic modeling of controlled release from poly-styrene-co-4-vinylpyridine microspheres," *J. Controlled Release* 32:139–146.

Shen, C., Sudol, E. D., El-Aaser, M. S. (1993) "Control of particle size in dispersion polymerization of methyl methacrylate," *J. Polym. Sci. Part A: Polym. Chem.* 31:1393–1402.

Shen, C., Sudol, E. D., El-Aaser, M. S. (1994) "Dispersion polymerization of methyl methacrylate: Mechanism of particle formation," *J. Polym. Sci. Part A: Polym. Chem.* 32:1087–1100.

Spenlehauer, G. Veillard, M., Benoit, J. P. (1986) "Formation and characterization of cisplatin loaded poly(d,l-lactide) microspheres for chemoembolization" *J. Pharm. Sci.* 75:750–755.

Trissel, L. A. (1994) *Handbook on Injectable Drugs,*($8^{th}$ ed.), American Society of Hospital Pharmacists, Inc.

Tuncel, A., Kahraman, R., Piskin, E. (1994) "Monosize polystyrene latices carrying functional groups on their surfaces," *J. Appl. Polym. Sci.* 51:1485–1498.

Uglestad, J., Mork, P. C. (1980) "Swelling of oligomer-polymer particles. New methods of preparation of emulsions and polymer dispersions," *Adv. in Colloid and Interface Sci.* 13:101–140.

Volk, T., Jahde, E., Fortmeyer, H. P., Glusenkamp, K. H., Rajewsky, M. F. (1993) "pH in human tumor xenografts: effect of intravenous administration of glucose" *Br. J. Cancer* 68:492–500.

Ward, E. S., Sigurdson, E. R., Tremiterra, S., Lincer, R., Chapman, D., Niedzwiecki, D. (1992) "Adjuvant chemotherapy for colorectal hepatic metastases: role of route of administration and timing," *Surgical Oncology* 1:87–95.

We claim:

1. A method of treating a patient having a tumor, said method comprising administering to the patient an effective amount of pH-sensitive microspheres, wherein said microspheres comprise a cross-linked polymer gel comprising ethyl methacrylate, diethyl aminoethyl methacrylate, and divinyl benzene, wherein said microspheres contain a substance selected from the group consisting of cytotoxic agents, chemotherapeutic agents, and radionuclides, and wherein said microspheres are capable of releasing said substance at a pH range associated with the tumor microenvironment, over a period of days.

2. The method of claim 1, wherein said microspheres are administered to the patient by injection in a blood vessel proximate to said tumor.

3. The method of claim 1, wherein said tumor is a hepatic tumor.

4. The method of claim 1, wherein the mole percent ratio of said ethyl methacrylate in said microspheres is in the range of about 50 to about 65, wherein the mole percent ratio of said diethyl aminoethyl methacrylate in said microspheres is in the range of about 34 to about 49, and wherein the mole percent ratio of divinyl benzene in said microspheres is in the range of about 1 to about 15.

5. The method of claim 4, wherein the mole percent ratio of said ethyl methacrylate in said microspheres is about 50, wherein the mole percent ratio of said diethyl aminoethyl methacrylate in said microspheres is about 49, and wherein the mole percent ratio of said divinyl benzene in said microspheres is about 1.

6. The method of claim 2, wherein said blood vessel is the hepatic artery.

7. The method of claim 1, wherein said microspheres are monodisperse.

8. A method of treating a tumor comprising administering pH-sensitive microspheres in a blood vessel suitable for carrying said microspheres to said tumor, wherein said microspheres comprise a cross-linked polymer gel comprising ethyl methacrylate, diethyl aminoethyl methacrylate, and divinyl benzene, wherein said microspheres contain a substance selected from the group consisting of cytotoxic agents, chemotherapeutic agents, and radionuclides, and wherein said microspheres are capable of releasing said substance at a pre-determined pH, over a period of days.

9. The method of claim 8, wherein said microspheres.

10. A pH-sensitive microsphere comprising a cross-linked polymer gel comprising ethyl methacrylate, diethyl aminoethyl methacrylate, and divinyl benzene, wherein said pH-sensitive microsphere is loaded with a substance selected from the group consisting of cytotoxic agents, chemotherapeutic agents, and radionuclides, and wherein said pH-sensitive microsphere is capable of effectively releasing said substance at a predetermined pH, over a period of days.

11. The microsphere of claim 10, wherein said microsphere effectively release said substance at a pH of between about 6.0 and about 7.4.

12. The microsphere of claim 10, wherein said microsphere effectively releases said substance at a pH of between about 6.3 and about 7.0.

13. The microsphere of claim 10, wherein said microsphere effectively releases said substance at a pH of between about 6.5 and about 7.0.

14. The microsphere of claim 10, wherein said 50% of said substance is released and about 50% of said substance remains to be released when said microsphere is exposed to a pH of about 6.8 for a period of 14 days.

15. The microsphere of claim 10, wherein the weight percentage of said substance loaded in said microsphere is up to about 20%.

16. The microsphere of claim 10, wherein the mole percent ratio of said ethyl methacrylate in said microsphere is in the range of about 50 to about 65, wherein the mole percent ratio of said diethyl aminoethyl methacrylate in said microsphere is in the range of about 34 to about 49, and wherein the mole percent ratio of said divinyl benzene in said microsphere is in the range of about 1 to about 15.

17. The microsphere of claim 16, wherein the mole percent ratio of said ethyl methacrylate in said microsphere is about 50, wherein the mole percent ratio of said diethyl aminoethyl methacrylate in said microsphere is about 49, and wherein the mole percent ratio of said divinyl benzene in said microsphere is about 1.

18. The microsphere of claim 10, wherein said microsphere has a diameter of between about 4 µm and about 150 µm.

19. The microsphere of claim 10, wherein said microsphere has a diameter of between about 10 µm and about 50 µm.

20. The microsphere of claim 10, wherein said microsphere has a diameter of between about 25 μm and about 35 μm.

21. A composition comprising a plurality of monodisperse pH-sensitive microspheres, wherein said pH-sensitive microspheres comprise a cross-linked polymer gel comprising ethyl methacrylate, diethyl aminoethyl methacrylate, and divinyl benzene, wherein said pH-sensitive microspheres are loaded with a substance selected from the group consisting of cytotoxic agents, chemotherapeutic agents, and radionuclides, and wherein said pH-sensitive microspheres are capable of effectively releasing said substance at a predetermined pH, over a period of days.

* * * * *

UNITED STATES PATENT AND TRADEMARK OFFICE
CERTIFICATE OF CORRECTION

PATENT NO. : 6,602,524 B2
DATED : August 5, 2003
INVENTOR(S) : Christopher D. Batich, Adam Leckey and J. Nicolas Vauthey It is certified that error appears in the above-identified patent and that said Letters Patent is hereby corrected as shown below:

Column 14,
Line 1, "30/0" should read -- 30/70 --.

Column 20,
Line 23, "wherein said microspheres" should read -- wherein said microspheres are monodisperse --.

Signed and Sealed this

Twenty-fourth Day of August, 2004

JON W. DUDAS
*Director of the United States Patent and Trademark Office*